(12) United States Patent
Griffith et al.

(10) Patent No.: US 11,826,540 B2
(45) Date of Patent: Nov. 28, 2023

(54) FLEXIBLE CAP FOR CONICAL CONNECTORS

(71) Applicant: Avent, Inc., Alpharetta, GA (US)

(72) Inventors: Nathan Griffith, Johns Creek, GA (US); Neil M. Becker, Alpharetta, GA (US)

(73) Assignee: Avent, Inc., Alpharetta, GA (US)

( * ) Notice: Subject to any disclaimer, the term of this patent is extended or adjusted under 35 U.S.C. 154(b) by 0 days.

(21) Appl. No.: 17/717,450

(22) Filed: Apr. 11, 2022

(65) Prior Publication Data

US 2022/0226630 A1 Jul. 21, 2022

Related U.S. Application Data

(62) Division of application No. 15/774,329, filed as application No. PCT/US2015/062977 on Nov. 30, 2015, now Pat. No. 11,324,938.

(51) Int. Cl.
*A61M 39/02* (2006.01)
*A61M 39/10* (2006.01)
*A61M 39/20* (2006.01)

(52) U.S. Cl.
CPC ........ *A61M 39/20* (2013.01); *A61M 39/1011* (2013.01); *A61M 2039/1033* (2013.01);
(Continued)

(58) Field of Classification Search
CPC .............. A61M 39/20; A61M 39/1011; A61M 2039/1033; A61M 2039/1038;
(Continued)

(56) References Cited

U.S. PATENT DOCUMENTS 3,307,552 A * 3/1967 Strawn .................. A61M 39/20
604/533
4,991,629 A 2/1991 Ernesto et al.
(Continued)

FOREIGN PATENT DOCUMENTS

DE     102 47 963 A1    5/2004
DE  10 2009 044319 A1   2/2011
(Continued)

OTHER PUBLICATIONS

International Search Report and Written Opinion for PCT/US2015/062977, dated Apr. 1, 2016, 13 pages.

*Primary Examiner* — Theodore J Stigell
(74) *Attorney, Agent, or Firm* — Dority & Manning, P.A.

(57) ABSTRACT

The present disclosure is directed to a flexible cap for a medical fitting, such as a luer-lock fitting. The flexible cap includes a cap component defining a top surface, a cylindrical wall extending opposite from the top surface of the cap component, and an inner sealing surface. The cylindrical wall defines a hollow interior configured to receive an internal tapered sealing wall of a male connector of the medical fitting so as to form a seal with an outer surface of the tapered sealing wall. Further, the inner sealing surface of the flexible cap is configured within the hollow interior. Thus, when the tapered sealing wall of the male connector of the medical fitting is received within the hollow interior of the cylindrical wall, the inner sealing surface of the flexible cap seals the fluid passageway of the tapered sealing wall.

12 Claims, 4 Drawing Sheets

(52) U.S. Cl.
CPC ............... *A61M 2039/1038* (2013.01); *A61M 2039/1044* (2013.01); *A61M 2205/582* (2013.01)

(58) Field of Classification Search
CPC .... A61M 2039/1044; A61M 2205/582; A61M 2005/3104; A61M 2005/3106
See application file for complete search history.

(56) References Cited

U.S. PATENT DOCUMENTS

| | | |
|---|---|---|
| 5,496,288 A | 3/1996 | Sweeney |
| 5,807,345 A | 9/1998 | Grabenkort |
| 5,855,230 A | 1/1999 | Guala et al. |
| 8,192,421 B2 | 6/2012 | Lopez et al. |
| 10,668,263 B2 | 6/2020 | Ingram et al. |
| 2011/0139830 A1 | 6/2011 | Hasegawa et al. |

FOREIGN PATENT DOCUMENTS

| | | |
|---|---|---|
| EP | 2 266 646 A1 | 12/2010 |
| EP | 2 444 117 A1 | 4/2012 |
| JP | 2002153539 A | 5/2002 |
| WO | WO 95/04569 A1 | 2/1995 |
| WO | WO 96/14100 A1 | 5/1996 |
| WO | WO 00/24442 A1 | 5/2000 |
| WO | WO 2014/159346 A1 | 10/2014 |
| WO | WO-2014159346 * | 10/2014 |
| WO | WO 2015/127285 A1 | 8/2015 |

\* cited by examiner

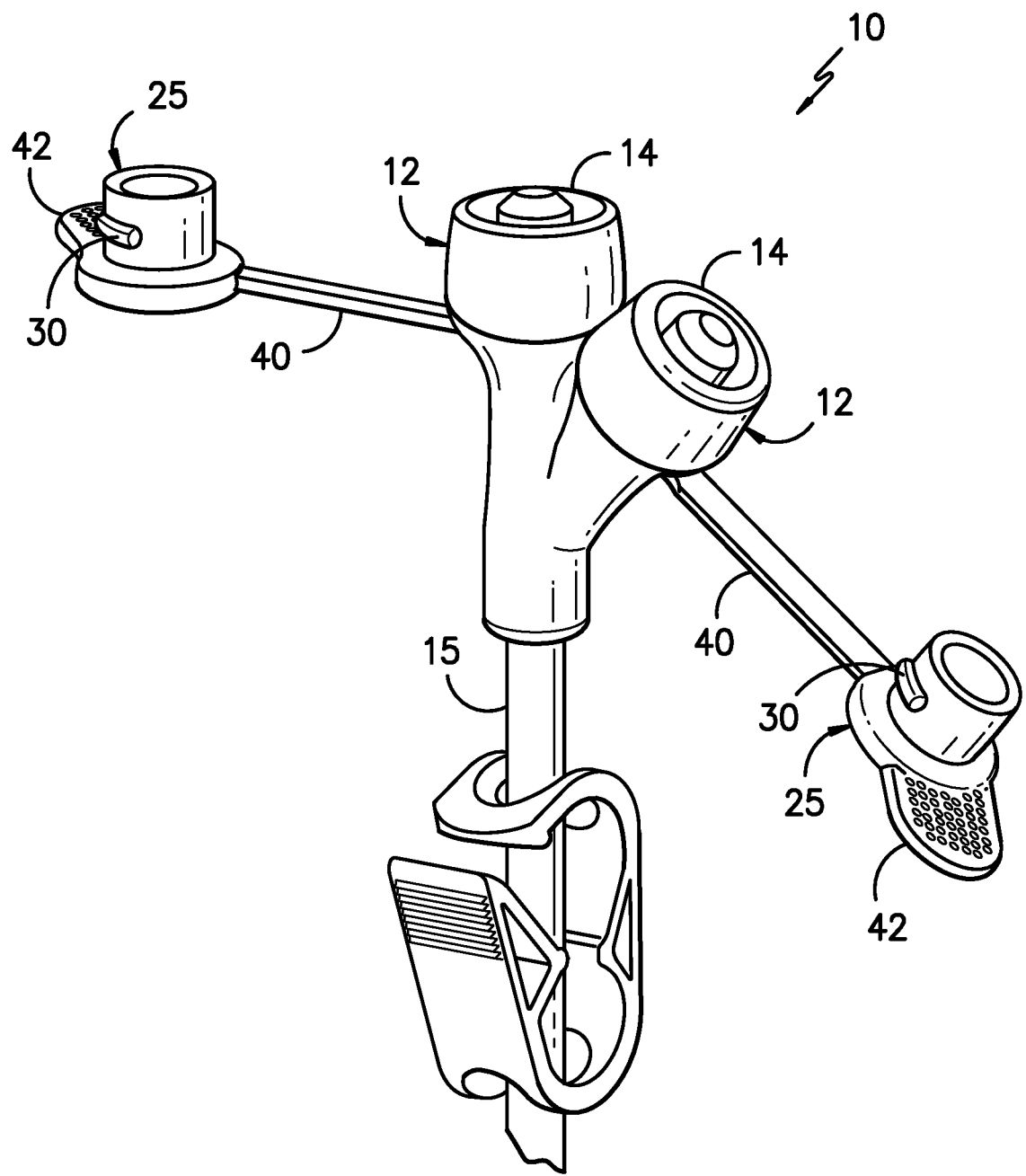
FIG. -1-

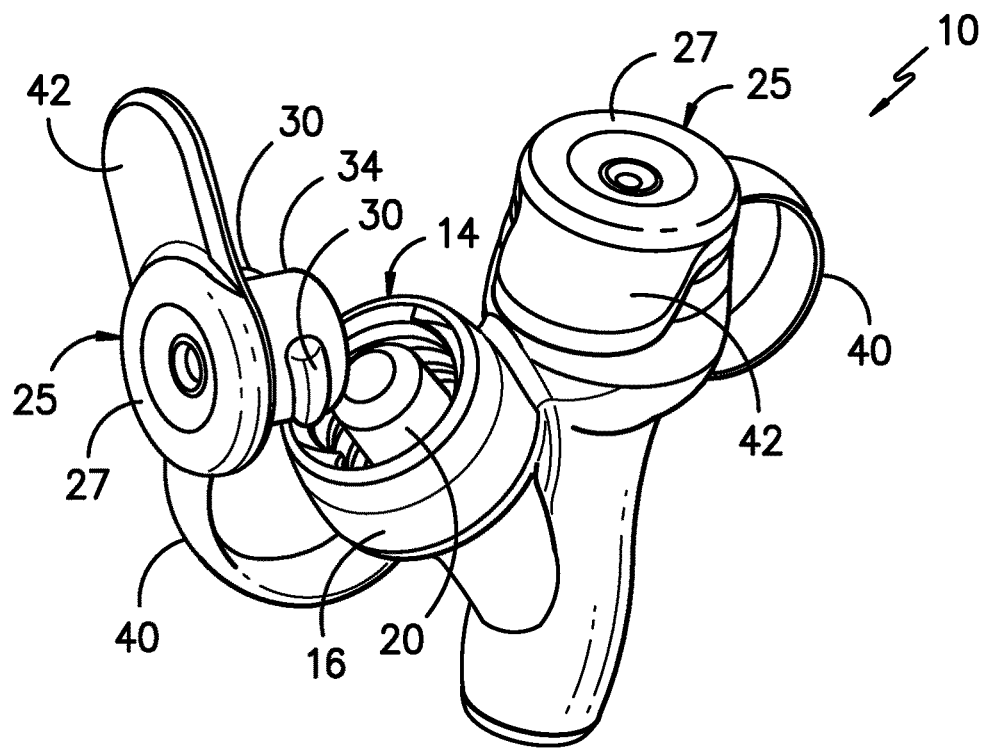
FIG. -2-
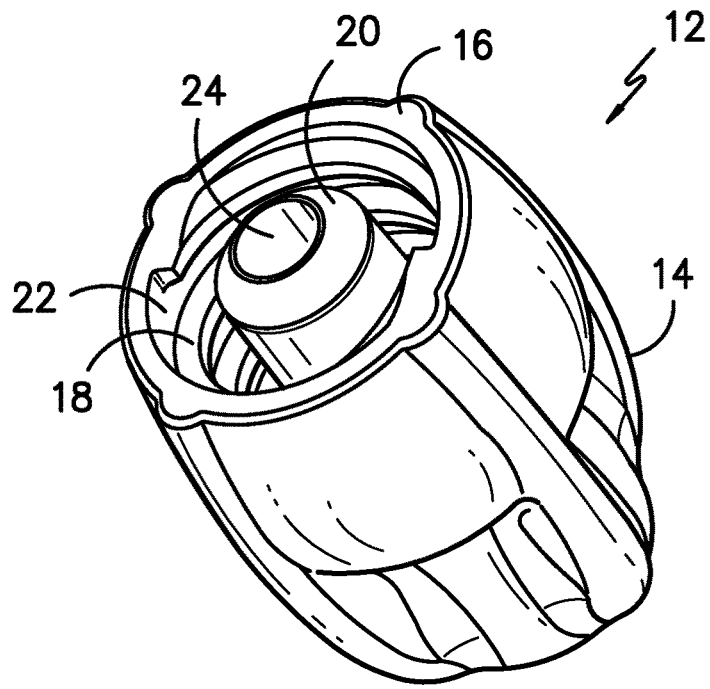
FIG. -3-

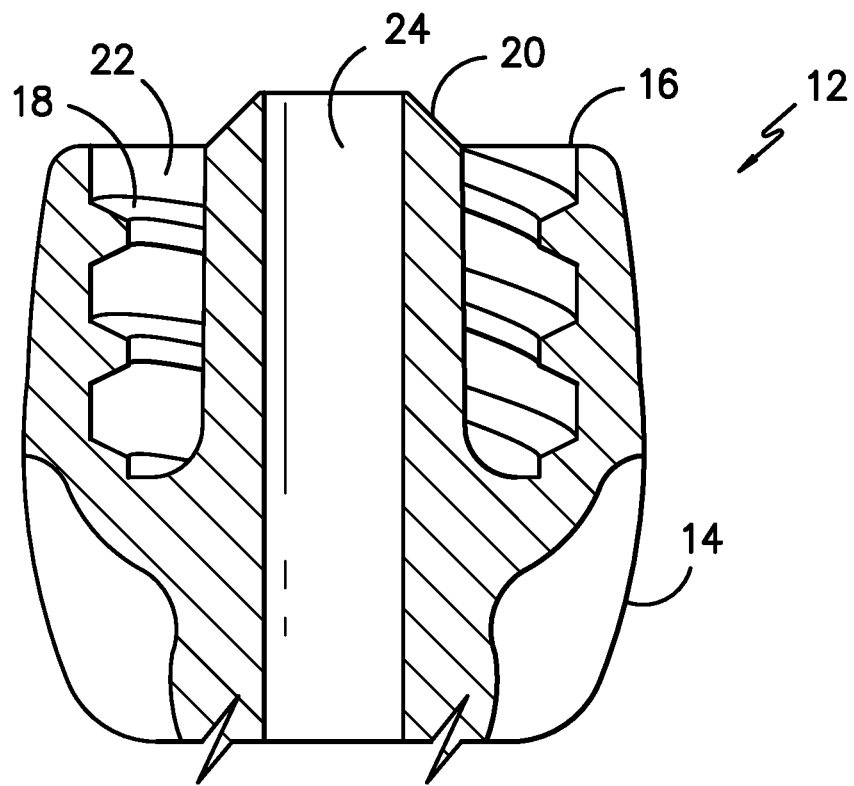
FIG. -4-
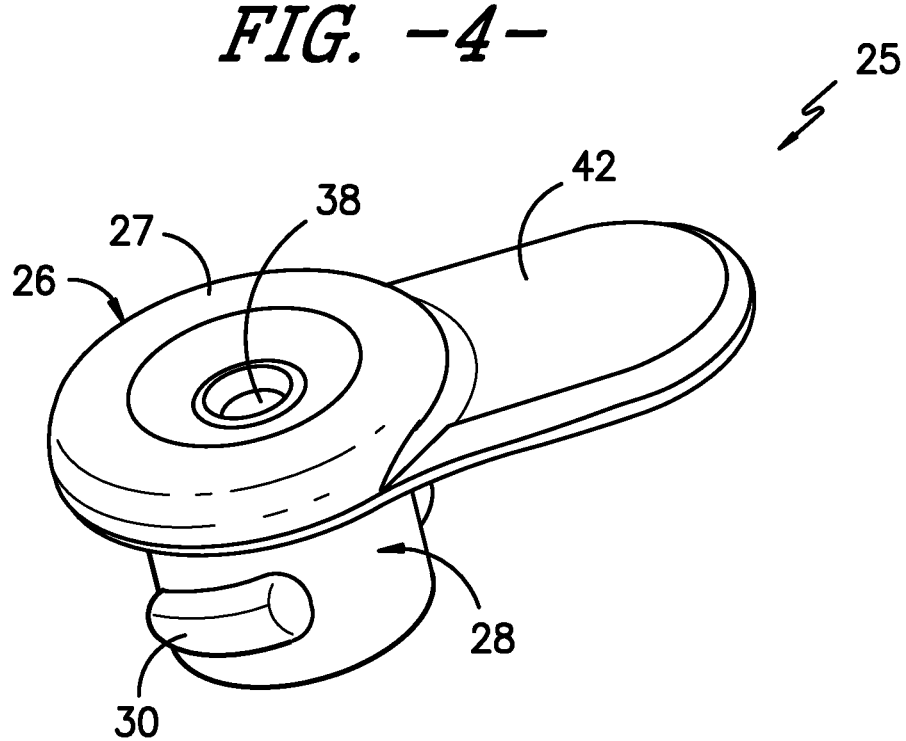
FIG. -5-

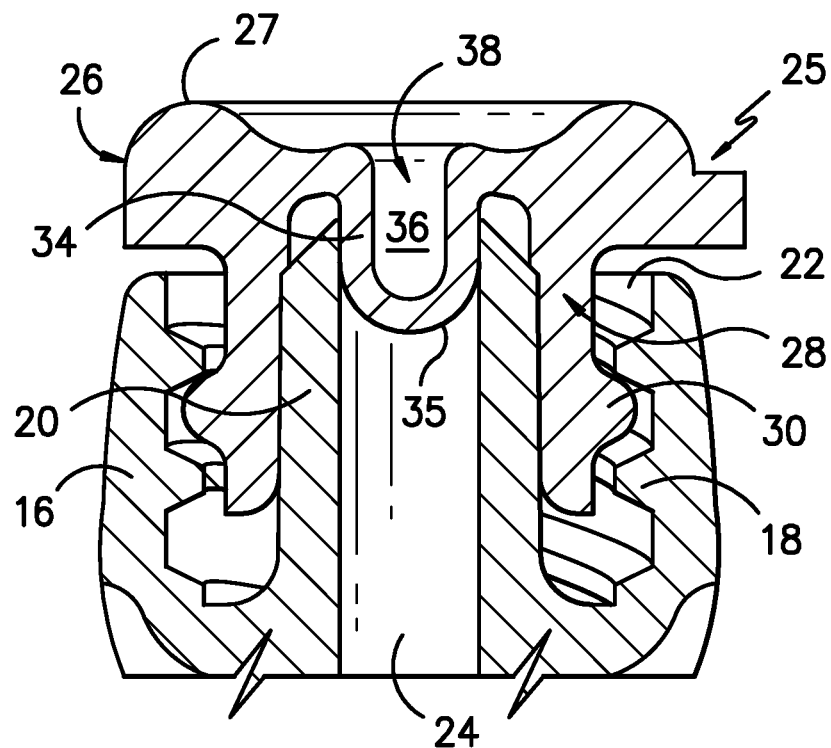
FIG. -6-
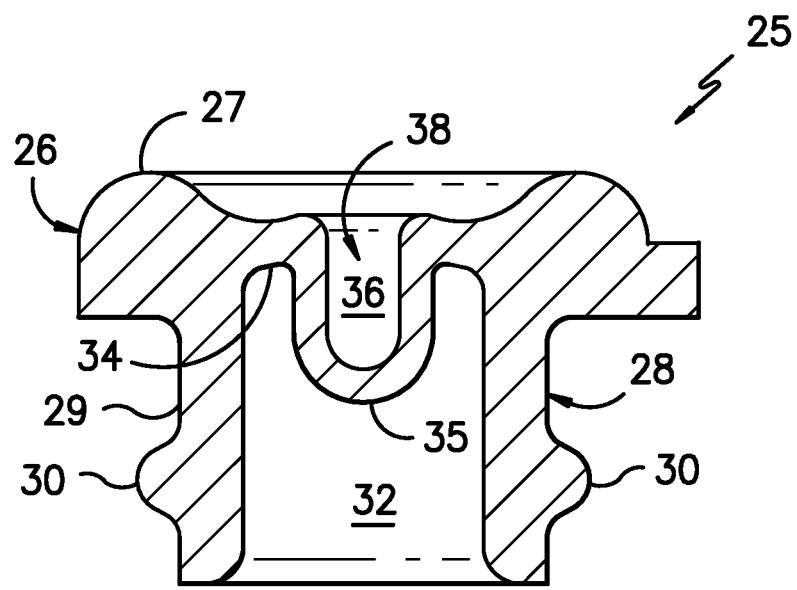
FIG. -7-

FLEXIBLE CAP FOR CONICAL CONNECTORS

RELATED APPLICATIONS

The present application is a divisional of and claims priority to U.S. application Ser. No. 15/774,329, which was filed on May 8, 2018, which is the national stage entry of International Patent Application No. PCT/US2015/062977, which was filed on Nov. 30, 2015, the entire contents of which are incorporated herein in their entirety by reference hereto.

FIELD OF THE INVENTION

The present invention relates in general to fittings or connectors for medical devices, and more particularly to a flexible cap for conical connectors of medical devices.

BACKGROUND OF THE INVENTION

International Standard Organization (ISO) 80369 is a new standard for medical device connections designed to prevent common connection errors in patient care. Many of the new connectors detailed in this standard utilize a conical sealing surface surrounded by a threaded collar. One example of this type of connector is a luer-lock fitting.

Luer-lock fittings for medical devices typically have a tubular body at one end a Luer cone connector at an opposing end. More specifically, medical fittings generally include threaded locking 'luer' designs having male and female connectors with corresponding threaded collars. The luer cone connector is coaxially surrounded by a cup-like inner threaded attachment element and a detachable cap sealingly connected axially over the Luer cone connector.

Thus, the detachable cap is configured to prevent undesirable flow of therapeutic fluids, gases, and/or bodily fluids from flowing from the fitting when not in use. Most existing cap designs utilize the geometry of the opposing connector. For example, a cap for the male connector generally corresponds to the geometry of the female connector design. Thus, a user is required to twist the cap into place on the male connector. Depending on the use, a twist cap can make certain medical procedures that utilize such luer-lock fittings more complex. Further, some twist caps include a tether which can prevent effective rotation of the cap. As such, in many instances, the tether must be a separate component from the cap.

In view of the above, push-caps are also known for preventing undesirable flow of therapeutic fluids, gases, and/or bodily fluids from flowing from such fittings when not in use. Though push caps can provide an enhanced user experience by simplifying use during a medical procedure, known push caps can become unintentionally dislodged. Further, known push caps may not provide proper sealing for medical fittings having a conical surface and locking collar.

In view of the aforementioned, an improved cap for a conical connector that prevents undesirable fluid and/or gas leaks would be welcomed in the art. Thus, the present disclosure is directed to a flexible cap for a conical fitting or connector that provides a robust and effective seal against fluid or gas leakage.

BRIEF SUMMARY OF THE INVENTION

Aspects and advantages of the invention will be set forth in part in the following description, or may be obvious from the description, or may be learned through practice of the invention.

In one aspect, the present disclosure is directed to a flexible cap for a male connector of a medical fitting. The male connector has an outer cylindrical locking collar and an internal tapered sealing wall having a fluid passageway therein. An internal cavity is defined between the outer locking collar and the tapered sealing wall. The flexible cap includes a cap component defining a top surface, a cylindrical wall, and an inner sealing surface. The cylindrical wall and the inner sealing surface are opposite from the top surface. Further, the cylindrical wall defines a hollow interior configured to receive the tapered sealing wall of the male connector so as to form a seal with an outer surface of the tapered sealing wall. In addition, the inner sealing surface is configured within the hollow interior of the cylindrical wall. Thus, when the tapered sealing wall of the male connector is received within the hollow interior of the cylindrical wall, the inner sealing surface is configured to seal the fluid passageway of the tapered sealing wall. In certain embodiments, the medical fitting may be a luer-lock fitting although it should be understood by those of ordinary skill in the art that the medical fitting may include any medical device connector having a tapered sealing surface and a threaded locking collar.

In one embodiment, the inner sealing surface may include a protrusion configured to fit at least partially within the fluid passageway so as to seal the fluid passageway. More specifically, the protrusion may be a dome, cone, cylinder, rib, or similar. Thus, the protrusion is configured to seal the fluid passageway when fluid pressure is applied. In addition, in certain embodiments, the protrusion may have a hollow cross-section or a solid cross-section. Thus, in such embodiments, the hollow cross-section of the protrusion may extend from the top surface of the cap component so as to define an open recess on the top surface of the cap component. As such, the recess may be open to the atmosphere such that it can deform in response to pressure from the fluid passageway so as to frictionally engage the walls thereof.

In another embodiment, the outer locking collar of the male connector has internal threads. Thus, in certain embodiments, the cylindrical wall of the flexible cap may include at least one rib on an exterior surface thereof. As such, the rib(s) of the flexible cap may be configured to engage the internal threads of the male connector. More specifically, in particular embodiments, the cylindrical wall of the flexible cap may include opposing ribs on opposite sides thereof.

In additional embodiments, the flexible cap may also have a tether. More specifically, in certain embodiments, the tether may be integral with the cap component or any other portion of the flexible cap. Alternatively, the tether may be a separate component that can be attached to the cap component. In still another embodiment, the cap component may include a pull tab configured to assist a user with removing the cap from the male connector.

In further embodiments, the flexible cap may be constructed of any suitable flexible or semi-flexible materials. For example, in certain embodiments, the flexible cap may be constructed of polyurethane, neoprene, synthetic rubber, latex, silicone, or similar, or combinations thereof.

In another aspect, the present disclosure is directed to a medical fitting for a medical device. The fitting includes a male connector and a flexible cap. The male connector has an outer locking collar and an internal tapered sealing wall. Further, the outer locking collar and the tapered sealing wall define an internal cavity therebetween. In addition, the tapered sealing wall defines a fluid passageway therethrough. Moreover, the internal cavity is configured to receive a female connector during use, and the flexible cap when not in use. The flexible cap includes a cap component defining a top surface, a cylindrical wall, and an inner sealing surface. Further, the cylindrical wall and the inner sealing surface are opposite from the top surface. Moreover, the cylindrical wall defines a hollow interior configured to receive the tapered sealing wall of the male connector so as to form a seal with an outer surface of the tapered sealing wall. In addition, the inner sealing surface is configured within the hollow interior of the cylindrical wall. Thus, when the tapered sealing wall of the male connector is received within the hollow interior of the cylindrical wall, the inner sealing surface seals the fluid passageway of the tapered sealing wall. It should also be understood that the medical fitting may further include any of the additional features as described herein.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 1 illustrates a perspective view of one embodiment of a medical device having double luer fittings according to the present disclosure;

FIG. 2 illustrates a detailed, perspective view of one embodiment of a medical device having double luer fittings according to the present disclosure;

FIG. 3 illustrates a perspective view of one embodiment of a male connector of a luer fitting according to the present disclosure;

FIG. 4 illustrates a cross-sectional view of the male connector of FIG. 3;

FIG. 5 illustrates a perspective view of one embodiment of a flexible cap for a male connector of a luer fitting according to the present disclosure;

FIG. 6 illustrates a cross-sectional view of one embodiment of a flexible cap inserted into a male connector of a luer fitting according to the present disclosure; and FIG. 7 illustrates a cross-sectional view of one embodiment of a flexible cap for a male connector of a luer fitting according to the present disclosure.

DETAILED DESCRIPTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Generally, the present disclosure is directed to a flexible cap for a medical fitting, such as luer fitting. More specifically, the cap includes a cap component defining a top surface, a cylindrical wall extending opposite from the top surface of the cap component, and an inner sealing surface. The cylindrical wall defines a hollow interior configured to receive an internal tapered sealing wall of a male connector of the medical fitting so as to form a first seal with the tapered sealing wall. Further, the inner sealing surface is configured within the hollow interior of the cylindrical wall such that, when the tapered sealing wall of the male connector is received within the hollow interior, the inner sealing surface provides a second seal with the fluid passageway of the tapered sealing wall. More specifically, in one embodiment, the inner sealing surface may include a protrusion, e.g. a dome, configured to fit at least partially within the fluid passageway so as to seal the fluid passageway when fluid pressure is applied.

The present disclosure provides many advantages not present in the prior art. For example, the push-in cap of the present disclosure reduces cost and complexity of typical medical devices that utilize medical fitting, such as luer-lock fittings. In addition, the flexible cap of the present disclosure provides an enhanced user experience that requires less effort during use over twist-on caps. Moreover, the flexible cap of the present disclosure effectively seals to the tapered surfaces of the conical male connector of medical fittings while also remaining resistant to unintentional dislodgement.

Referring now to the drawings, FIGS. 1 and 2 illustrates a medical device 10 for delivering a discrete amount of medication, gas, internal nutrition, drug, or other fluid to a patient, e.g. in order to raise its concentration in the patient's blood to an effective level. Thus, the medical device 10 may be connected to a fluid or gas delivery device (not shown) that delivers a treatment fluid to a patient via one or more ports or medical fittings 12. More specifically, as shown the medical fittings 12 are luer-lock fittings that are configured to transport the treatment fluid or gas through a tube 15 and subsequently to a catheter or syringe (not shown). For example, as shown, the medical device 10 includes two luer fittings 12, i.e. to deliver two separate treatment fluids to a patient. In alternative embodiments, the medical device 10 may include a single luer fitting 12. It should be understood that a medical device 10 having any number of luer fittings 12 is within the spirit and scope of the invention.

Referring now to FIGS. 3, 4, and 6, the medical fitting 12 includes a male connector 14 having an outer locking collar 16 and an internal tapered sealing wall 20. As shown, the outer locking collar 16 and the tapered sealing wall 20 define an internal cavity 22 therebetween. Thus, the tapered sealing wall 20 of the male connector 14 can be inserted into a female connector (not shown) and the female connector may be secured within the internal cavity 22 of the male connector 14. More specifically, as shown, the outer locking collar 16 of the male connector 14 may have internal threads 18. Thus, in such embodiments, the male connector 14 may be secured within the female connector via the threads 18 during use. In addition, the tapered sealing wall 20 is generally tapered so that it can be easily inserted to the female connector during use. Further, the tapered sealing wall 20 defines a fluid passageway 24 therethrough, i.e. for delivering treatment fluid to a patient. As such, when the male and female connectors are engaged, treatment fluid is delivered through the medical fitting 12 via a fluid delivery device to the patient.

When the medical device 10 is not in use, i.e. the female connector is not engaged with the male connector 14, the medical fitting 12 may include a flexible cap 25 configured to fit within the internal cavity 22 of the male connector 14. For example, as shown in FIGS. 5-7, the flexible cap 25 includes a cap component 26 defining a top surface 27. Further, as shown, the flexible cap 25 includes a cylindrical wall 28 extending opposite from the top surface 27 of the cap component 26. In addition, as shown, the cylindrical wall 28 defines a hollow interior 32 configured to receive the tapered sealing wall 20 of the male connector 14. Thus, when engaged with the tapered sealing wall 20, the cylindrical wall 28 is configured expand so as to form a seal with an outer surface 21 of the tapered sealing wall 20. Thus, the flexible cap 25 is configured to resist unintentional dislodgement of the cap 25.

In addition, the flexible cap 25 may include a second sealing surface 34 having a protrusion 35 configured to fit within the fluid passageway 24 of the internal tapered sealing wall 20. For example, in one embodiment, the protrusion 35 may have a domed geometry that fits within the fluid passageway 24 of the internal tapered sealing wall 20. More specifically, in one embodiment, the inner sealing surface 34 may include a dome 35 configured to fit at least partially within the fluid passageway so as to seal the fluid passageway when fluid pressure is applied. Thus, the double-seal configuration of the flexible cap 25 is configured to create a wedge around the full circumference of the male connector 14, thereby providing a robust and effective seal against fluid or gas leakage.

More specifically, as shown in FIGS. 5-7, the dome 35 of the second or inner sealing surface 34 extends within the hollow interior 32 of the cylindrical wall 28. As such, when the tapered sealing wall 20 of the male connector 14 is received within the hollow interior 32 of the cylindrical wall 28, the dome 35 of the inner sealing surface 34 is configured to seal the fluid passageway 24 of the tapered sealing wall 20, e.g. when fluid pressure is applied to the cap 25. Thus, in certain embodiments, the dome 35 of the inner sealing surface 34 is configured to seal the fluid passageway 24 so as to prevent liquids or gases from exiting therefrom.

In addition, in particular embodiments, the dome 35 may have a substantially hollow cross-section 36. Thus, in such embodiments, the hollow cross-section 36 of the dome 35 may extend from the top surface 27 of the cap component 26 so as to define first open recess the top surface 27. In other words, in certain embodiments, the first open recess is open to the atmosphere such that the dome 35 can deform in response to pressure from the fluid passageway so as to frictionally engage the walls of the fluid passageway 24. More specifically, as shown in FIG. 6, the hollow cross-section extends from the first open recess defined in the top surface 27 to a distal end of the dome 35 so as to define a second open recess 38 that connects to the first open recess. In alternative embodiments, the protrusion 35 may have a solid cross-section.

Additionally, as shown in FIGS. 2 and 5-7, the cylindrical wall 28 of the flexible cap 25 may include at least one rib 30 on an exterior surface 29 thereof. As such, the rib(s) 30 of the flexible cap 25 may be configured to engage or mate with the internal threads 18 of the male connector 14. More specifically, in particular embodiments, the cylindrical wall 28 of the flexible cap 25 may include opposing ribs 30 on opposite sides thereof. Thus, the rib(s) 30 are configured to provide tactile feedback to a user during insertion of the cap 25 within the internal cavity 22 of the male connector 14.

Referring specifically to FIGS. 1, 2, and 5, the flexible cap 25 may also have a tether 40 configured to maintain attachment of the flexible cap 25 to the medical device 10. In certain embodiments, as shown, the tether 40 may be integral with the cap component 26 of the flexible cap 25 (or any other portion of the flexible cap 25). In alternative embodiments, the tether 40 may be a separate component from the cap component 26 of the flexible cap 25 that is later attached to the cap 25.

In another embodiment, as shown in FIGS. 1, 2, and 5, the cap component 26 of the flexible cap 25 may also include a pull tab 42 configured to facilitate removal of the cap 25 from the male connector 14 of the medical fitting 12, e.g. by a user.

In further embodiments, the flexible cap 25 may be constructed of any suitable flexible or semi-flexible materials. For example, in certain embodiments, the flexible cap 25 may be constructed of polyurethane, neoprene, synthetic rubber, latex, silicone, or similar, or combinations thereof. In addition, the flexible cap 25 of the present disclosure can be constructed of the same molded part as the tether and/or the male connector 14, thereby reducing the cost and number of components required to manufacture a medical fitting 12. As such, the present disclosure provides an enhanced user experience as less dexterity is required to activate the flexible cap 25 as compared to a twist-on cap.

While various patents have been incorporated herein by reference, to the extent there is any inconsistency between incorporated material and that of the written specification, the written specification shall control. In addition, while the disclosure has been described in detail with respect to specific embodiments thereof, it will be apparent to those skilled in the art that various alterations, modifications and other changes may be made to the disclosure without departing from the spirit and scope of the present disclosure. It is therefore intended that the claims cover all such modifications, alterations and other changes encompassed by the appended claims.

What is claimed is:

1. A flexible cap for a male connector of a medical fitting, the male connector having an outer locking collar and an internal tapered sealing wall that defines an internal cavity therebetween, the outer locking collar of the male connector comprising internal threads, the internal tapered sealing wall defining a fluid passageway, the flexible cap being a push-in cap, the push-in cap comprising:

a cap component defining a top surface;

a cylindrical wall extending opposite from the top surface of the cap component, the cylindrical wall defining a hollow interior configured to receive the internal tapered sealing wall of the male connector so as to form a seal with an outer surface of the internal tapered sealing wall, wherein the cylindrical wall is expandable, wherein the cylindrical wall further comprises at least one rib on an exterior surface thereof, wherein the at least one rib is configured to engage the internal threads of the outer locking collar of the male connector when the cylindrical wall expands; and an inner sealing surface configured within the hollow interior, wherein, when the internal tapered sealing wall of the male connector of the medical fitting is received within the hollow interior of the cylindrical wall, the inner sealing surface seals the fluid passageway of the internal tapered sealing wall.

2. The flexible cap of claim 1, wherein the inner sealing surface comprises a protrusion configured to fit at least partially within the fluid passageway so as to seal the fluid passageway.

3. The flexible cap of claim 2, wherein the protrusion comprises a dome configured to fit at least partially within the fluid passageway so as to seal the fluid passageway.

4. The flexible cap of claim 2, wherein the protrusion comprises a hollow cross-section.

5. The flexible cap of claim 4, wherein the hollow cross-section extends from the top surface of the cap component so as to define an open recess on the top surface of the cap component.

6. The flexible cap of claim 1, wherein the medical fitting comprises a leer-lock fitting.

7. The flexible cap of claim 1, wherein the at least one rib comprises opposing ribs on opposite sides of the cylindrical wall.

8. The flexible cap of claim 1, further comprising a tether.

9. The flexible cap of claim 8, wherein the tether is integral with the cap component.

10. The flexible cap of claim 1, wherein the cap component further comprises a pull tab.

11. The flexible cap of claim 1, wherein the flexible cap is constructed from at least one of polyurethane, neoprene, synthetic rubber, latex, or silicone.

12. The flexible cap of claim 1, wherein the at least one rib is configured to provide tactile feedback when the push-in cap is inserted within the internal cavity of the male connector.

* * * * *